United States Patent [19]

Tsirjulnikov et al.

[11] Patent Number: 4,953,542
[45] Date of Patent: Sep. 4, 1990

[54] DEVICE FOR TREATMENT OF SEXUAL IMPOTENCE IN HUMAN MALES

[76] Inventors: Moisei V. Tsirjulnikov, Vasilievsky ostrov, 15 linia, 14, kv. 8; Zinovy A. Zusmanovsky, 5-ya Sovetskaya ulitsa, 34, kv. 42, both of, Leningrad, U.S.S.R.

[21] Appl. No.: 271,958

[22] PCT Filed: Dec. 28, 1987

[86] PCT No.: PCT/SU87/00157
§ 371 Date: Sep. 26, 1988
§ 102(e) Date: Sep. 26, 1988

[87] PCT Pub. No.: WO88/05292
PCT Pub. Date: Jul. 28, 1988

[30] Foreign Application Priority Data

Jan. 27, 1987 [SU] U.S.S.R. .............................. 4185874

[51] Int. Cl.$^5$ ................................................ A61F 5/41
[52] U.S. Cl. ..................................................... 128/79
[58] Field of Search ............................................. 128/79

[56] References Cited

U.S. PATENT DOCUMENTS

| 4,362,152 | 12/1982 | Gorokhovsky | 128/79 |
| 4,429,689 | 2/1984 | Yanong | 128/79 |
| 4,672,954 | 6/1987 | Panzer | 128/79 |

FOREIGN PATENT DOCUMENTS

| 178044 | 3/1966 | U.S.S.R. | |
| 589978 | 1/1978 | U.S.S.R. | 128/79 |
| 2086230 | 5/1982 | United Kingdom | |

*Primary Examiner*—Cary E. Stone
*Attorney, Agent, or Firm*—Lilling and Lilling

[57] ABSTRACT

A device for treatment of sexual impotence in human males comprises parallel rods movably interconnected with a possibility of pivoting around their axes, each of the rods being connected to one of the ends of arcuate members which form a glans penis retainer shaped as curved plates, a control retainer and a penile base retainer. The free ends of the arcuate members of the penile base retainer are interconnected through an elastic member provided with a mechanism for reversible adjustment of the degree of its tension and having an eyelet made of the same material as the elastic member.

1 Claim, 1 Drawing Sheet

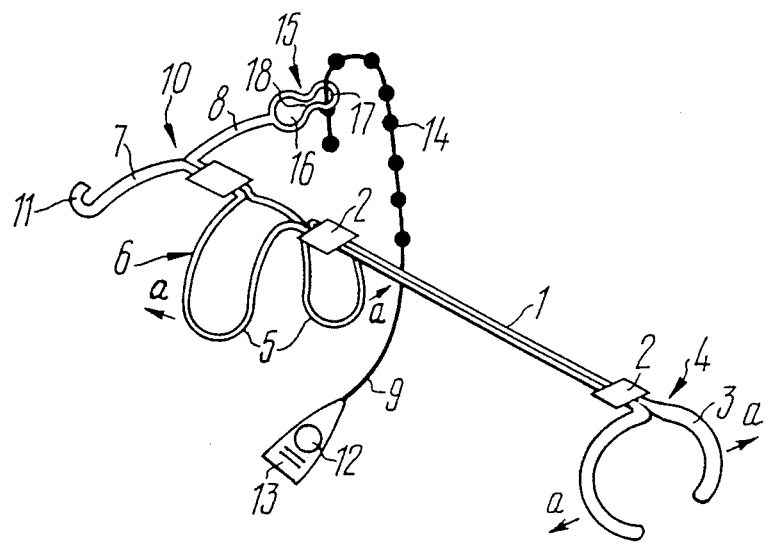

DEVICE FOR TREATMENT OF SEXUAL IMPOTENCE IN HUMAN MALES

FIELD OF THE INVENTION

The present invention relates generally to medicine and more specifically to devices for treatment of sexual impotence in human males.

DESCRIPTION OF THE PRIOR ART

There are widely known devices for treatment of sexual impotence in males acting by establishing conditions favourable for erection of a penis, comprising a holding rod articulated to a support ring and terminating in soft arcuate members.

One state-of-the-art device for treatment of sexual impotence in males (SU, A, 178,044) is known to comprise two rods adjacent to each other and coated with a common elastic sheathing. The distal ends of the rods terminate in arcuate members following the shape of the penile coronary sulcus and encompassing the glans penis on its proximal side with segments which form, when turned alongside with the adjustable portion, a support ring resting against the pubis.

A disadvantage of said device resides in the fact that it is impossible to adjust the degree of the glans penis compression depending on the degree of true penile erection in the course of sexual intercourse, as well as in sophisticated individual fitting-up of the device.

The aforesaid disadvantages are to some extent overcome in another device for treatment male weakness (SU, A, 589,978), comprising parallel rods movably interconnected with a possibility of pivoting around their axes, each of the rods being connected to one of the ends of the arcuate members that establish a retainer of the glans penis, a control retainer and a retainer of the penile base. The free ends of the arcuate members of the latter are interconnected through an elastic member having an eyelet adapted to interact with a hook fixed in position on the free end of one of the arcuate members of the penile base retainer.

The known device provides for graduated compression of the glans penis by the retainer lugs depending on the degree of penile erection which precludes painful sensations resulting from overcompression of the glans of an erect penis in the case of a full erection, whereby there is created an effect of freedom from any auxiliary appliances or aid devices.

However, said known device fails to provide maximum reliability of the glans penis fixation, since the fittings of the front retainer have a round cross-section, whereby its area of adherence to the penis is minimal and the elastic sheathing is liable to occur which might result in the glans penis escaping from the closed-up retainer. Another disadvantage inherent in the known device for treatment of sexual impotence in males resides in its being incapable of providing maximally accurate individual fitting-up of the device, i.e., the bracer can be adjusted for a smaller length only by cutting off an excess portion, which precludes restoration of the original bracer length in the case of an error.

A primary fitting-up of the device carried out on a non-erect penis might happen inadequately accurate when true erection of the penis occurs in the course of a sexual act. In the known device adjustment is performed by diminishing the length of the elastic element, which fails to provide a correct fitting-up and causes a discomforting sensation during the sexual intercourse, thereby affecting the efficiency of the treatment. In addition, a round cross-section of the glans penis retainer components might likewise inflict discomfort upon the patient in the course of penile erection due to a specific pressure exerted upon the penile tissues in the region of the sulcus of the penile corona. Nor can said round cross-section ensure a reliable fixation of the glans penis on account of too small a contact area of the arcuate members of the retainer with the skin surface of the penis, which tells extremely unfavourably on the treatment efficiency and causes distrust of a patient to this treatment method.

Furthermore, the eyelet secured at the end of the elastic member and made of an inelastic material offers additional discomfort for both of the partners of a sexual intercourse.

SUMMARY OF THE INVENTION

It is a primary object of the present invention to provide a device for treatment of sexual impotence in human males, which would be capable of ensuring a reversible adjustment of the degree of tension of the elastic member of the penile base retainer and a reduced specific pressure exerted on the penile tissues in the zone of the sulcus of the penile corona, as well as increased reliability of fixation of the glans of a non-erect penis.

The foregoing object is accomplished by a device, comprising parallel rods movably interconnected with a possibility of pivoting around their axes, each of the rods being connected to one of the ends of the arcuate members that form the glans penis retainer, the control retainer and the penile base retainer. The free ends of the arcuate members of the penile base retainer are interconnected through an elastic member having an eyelet adapted to interact with the hook secured on the free end of one of the arcuate members of the penile base retainer. According to the invention, the elastic member has a mechanism for reversible adjustment of the degree of its tension, the eyelet is made of the same material as the elastic member, and the arcuate members of the retainer are shaped as curved plates.

Such a construction arrangement of the device enables one to attain higher efficiency of treatment due to a possibility of accurately adjusting the degree of tension of the elastic member of the penile base retainer, a reduced specific pressure on the tissues of the penile corona sulcus, and increased reliability of fixation of the glans penis.

It is expedient that the mechanism of reversible adjustment be made as spheroid thickenings on the elastic member, which are adapted to interact with a lock situated at the free end of the other arcuate member of the penile base retainer and made as two holes interconnected through a recess, the diameter of one of said holes exceeding the diameter of the spheroid thickenings, and that of the other hole being smaller than the diameter of the thickenings.

Such an embodiment of the reversible adjustment mechanism provides an adequately accurate and quick adjustment of the degree of tension of the elastic member being in fact a simple construction arrangement.

BRIEF DESCRIPTION OF THE DRAWING

The essence and further advantages of the present invention will hereinafter be illustrated in the following detailed description thereof with due reference to the accompanying drawing, which represents a device for treatment of sexual impotence in human males, according to the invention.

DETAILED DESCRIPTION OF THE INVENTION

The device for treatment of sexual impotence in human males comprises two parallel rods 1 made of a metal wire and installed with a possibility of pivoting around their axes in sleeves 2. One of the ends of the rods 1 is connected to the ends of an arcuate member 3 which is made as a plate curved to suit the shape of the penile corona sulcus. Both of the arcuate members 3 in combination form a retainer 4 of the glans penis. In their middle portion the rods 1 are connected to arcuate members 5 which are curved into a loop whose semiarcs encompass the penis circumferentially to form a control retainer 6. The opposite end of each rod 1 is connected respectively to the ends of arcuate members 7,8 which form, together with an elastic member 9 made of rubber, a penile base retainer 10. The free end of the arcuate member 7 has a hook 11 adapted to interact with the hole of an eyelet 12 provided at one of the ends of the elastic member 9. The eyelet 12 is made integral with the elastic member 9 and has a holder 13. Spheroid thickenings 14 are provided at the other end of the elastic member 9 and adapted to interact with a lock 15 located at the free end of the arcuate member 8. The lock 15 is made as two holes 16, 17 interconnected through a recess 18. The diameter of the hole 16 exceeds that of the spheroid thickening 14 of elastic member 9, whereas the diameter of the hole 17 is smaller than the diameter of said thickening. The surfaces of the metallic components 1,2, 3, 4, 5, 7, and 8 are enclosed in an elastic sheathing.

The device of the invention functions as follows.

The device is fitted over a non-erect penis. The retainer 4 encompasses the penile corona sulcus, the control retainer 6 does so with the middle penile portion, while the penile base retainer 10 encompasses the radix penis behind the scrotum at the pubic bone through its arcuate members 7, 8 and the elastic member 9. At the same time, the eyelet 12 of the elastic member 9 is fitted, by the holder 13, onto the hook 11 of the arcuate element 7 and the degree of tension of the elastic member 9 is adjusted by selecting the appropriate spheroid thickening 14 engaged in the lock 15. The spheroid thickening 14 is fixed in place in the lock 15 as follows: the end of the elastic member 9 is inserted into the larger hole 16 at the level of the preselected spheroid thickening 14 and is moved along the recess 18 into the smaller hole 17, which holds the spheroid thickening 14 in position. When the length of the elastic member that determines the degree of its tension has been selected improperly the elastic member 9 is to be withdrawn in the reversed order, whereupon said member is either shortened or lengthened by selecting and fixing another spheroid thickening 14.

Thus, the penis assumes the position enabling the patient to perform a sexual intercourse without any discomforting sensation for either partner.

When true erection occurs during the sexual intercourse, the penis is enlarged diametrically and exerts pressure on the arcs of the retainer 6 (in the direction of the arrows a—a), which results in automatic opening, by virtue of pivoting the rods 1 around their axis, of the arcs 3 of the glans penis retainer 4 (in the direction of the arrows a—a), thus ensuring unobstructed enlargement of the penis to its natural erect size (both for length and diameter) without offering any discomfort for the male partner. When the degree of the penile erection relaxes during the sexual intercourse due to the fact that when fitted over the penis the elastic member 9 of the penile base retainer 10 is in somewhat stretched state, the elastic member causes the glans penis retainer 4, the control retainer 6, and the penile base retainer 10 to return to the original state synchronously, thus holding the penis in the erect position and enabling one to continue the sexual act. The same functional mechanism of the device makes continuation of the sexual intercourse possible in the case of premature ejaculation.

With the device fitted over the penis the latter is fully exposed to tactile sexual stimulation of the glans receptors.

The device operates on the feedback principle due to the provision of the retainer 6, which monitors the degree of dilation of the corpora cavernosa of the penis, thus establishing automatically the favourable conditions of enlarging the penis both in length and diameter during true erection occuring in the course of a sexual act and offering no discomfort either for the male or female partner. This in turn creates an effect of absence of a sex aid device. The device, according to the invention, holds the penis in position when the effect thereof is weakened in the course of the sexual act or after premature ejaculation, as well as renders a sexual intercourse practicable even in cases where the patient is completely devoid of an efficient function. When correctly fitted-up to a given patient, the device enables him to enjoy harmonious intimacy practically whenever necessary.

INDUSTRIAL APPLICABILITY

The invention disclosed herein can find application in treatment of sexual impotence in males predominantly of the functional (psychogenic) and functional-organic origin.

What is claimed is:

1. A device for treatment of sexual impotence in human males, comprising parallel rods movably interconnected with a possibility of pivoting around their axes; a retainer of the glans penis formed of arcuate members shaped as curved plates and one of the ends of the arcuate members of said retainer being connected to each of said parallel rods; a control retainer formed of arcuate members and one of the ends of the arcuate members of said control retainer being connected to each of said parallel rods; a retainer of the penile base formed of arcuate members, first ends of the arcuate members of said retainer of the penile base being connected to each of said parallel rods and a second end of a first of said arcuate members of said retainer of the penile base having a hook; an elastic member having an eyelet of the same material as the elastic member, said eyelet interacting with said hook, and said elastic member interconnecting said arcuate members of said retainer of the penile base; and a mechanism for reversible adjustment of the degree of tension of the elastic member made as spheroid thickenings provided on the elastic member and interacting with a lock located on a second end of a second of said arcuate members of the retainer of the penile base, said lock being made as first and second holes interconnected through a recess, the diameter of said first hole exceeding the diameter of the spheroid thickenings and the diameter of the second hole being smaller than that of the spheroid thickenings.

* * * * *